United States Patent
Kuranisi

(10) Patent No.: US 10,462,887 B2
(45) Date of Patent: Oct. 29, 2019

(54) RADIATION IRRADIATION DEVICE

(71) Applicant: FUJIFILM Corporation, Tokyo (JP)

(72) Inventor: Hideaki Kuranisi, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 237 days.

(21) Appl. No.: 15/623,388

(22) Filed: Jun. 15, 2017

(65) Prior Publication Data

US 2017/0374728 A1 Dec. 28, 2017

(30) Foreign Application Priority Data

Jun. 28, 2016 (JP) .................................. 2016-127430

(51) Int. Cl.
| | |
|---|---|
| *H05G 1/12* | (2006.01) |
| *A61B 6/00* | (2006.01) |
| *H05G 1/08* | (2006.01) |
| *H05G 1/14* | (2006.01) |
| *H05G 1/06* | (2006.01) |

(52) U.S. Cl.
CPC .............. *H05G 1/12* (2013.01); *A61B 6/4283* (2013.01); *A61B 6/44* (2013.01); *A61B 6/4405* (2013.01); *A61B 6/4458* (2013.01); *A61B 6/56* (2013.01); *A61B 6/587* (2013.01); *H05G 1/06* (2013.01); *H05G 1/08* (2013.01); *H05G 1/085* (2013.01); *H05G 1/14* (2013.01)

(58) Field of Classification Search
CPC .. H05G 1/12; H05G 1/06; H05G 1/08; H05G 1/085; H05G 1/14; A61B 6/4283; A61B 6/4405; A61B 6/4458; A61B 6/56; A61B 6/587; A61B 6/44
See application file for complete search history.

(56) References Cited

U.S. PATENT DOCUMENTS

| | | | |
|---|---|---|---|
| 6,563,717 B2 | 5/2003 | Lunding et al. | |
| 2013/0195248 A1* | 8/2013 | Rothschild | G01N 23/203 378/86 |
| 2015/0023468 A1* | 1/2015 | Zou | A61B 6/4405 378/62 |

FOREIGN PATENT DOCUMENTS

| | | | |
|---|---|---|---|
| JP | S6116498 | | 1/1986 |
| JP | H05315089 | | 11/1993 |
| JP | 2000150193 A | * | 5/2000 |
| JP | 2002175900 | | 6/2002 |
| JP | 2010244834 | | 10/2010 |
| JP | 2012243730 | | 12/2012 |

* cited by examiner

*Primary Examiner* — Kiho Kim
(74) *Attorney, Agent, or Firm* — JCIPRNET

(57) ABSTRACT

Provided is a radiation irradiation device that can improve the degree of freedom of an arm part and can reduce the number of noise suppression components, such as a ferrite core. A radiation irradiation device includes a radiation generating part having a radiation source that generates radiation; an arm part having the radiation generating part attached to one end thereof; and a main body part having the other end of the arm part connected thereto. The main body part has a power source part including a three-phase inverter circuit. The power source part supplies a three-phase alternating current voltage to the radiation generating part via the arm part.

15 Claims, 6 Drawing Sheets

RADIATION IRRADIATION DEVICE

CROSS-REFERENCE TO RELATED APPLICATIONS

The present application claims priority under 35 U.S.C. § 119 to Japanese Patent Application No. 2016-127430, filed on Jun. 28, 2016. Each of the above application(s) is hereby expressly incorporated by reference, in its entirety, into the present application.

BACKGROUND OF THE INVENTION

1. Field of the Invention

The present invention relates to a radiation irradiation device having an aim part provided with a radiation source.

2. Description of the Related Art

In the related art, portable radiation irradiation devices used in a case where a patient's radiation image are captured in operating rooms, examination rooms, or inpatient rooms have been suggested variously.

The portable radiation irradiation devices basically include a leg part enabled to travel by wheels, a main body part that houses a control part consisting of a battery for driving a radiation source, an electric circuit related to the driving of the radiation source, and the like and is held on the leg part, and an arm part connected to the main body part, and are configured by attaching the radiation source to a tip of the arm part.

When such radiation irradiation devices are used, a radiation irradiation device is first moved to the vicinity of a patient's bed. Next, the radiation source is moved to a desired position, and a radiation detector is moved to a desired position behind a subject. Then, in this state, the subject is irradiated with radiation by driving the radiation source, and a radiation image of the subject is acquired by detecting the radiation transmitted through the subject using the radiation detector.

SUMMARY OF THE INVENTION

Here, since radiation irradiation devices for general imaging among the radiation irradiation devices have a high X-ray tube voltage, a positive side power source and a negative side power source are separately provided with respect to a ground potential, and the respective power sources have ½ voltages on the negative side and the positive side. Accordingly, in many cases, a circuit configuration in which the withstand voltages of the respective power source can be reduced to ½ of the X-ray tube voltage is taken. For example, in a case where the X-ray tube voltage is 100 kV, a configuration in which power sources (+50 kV and −50 kV) are connected in series is used.

In this way, in a case where separate power sources are separately provided on the positive electrode side and the negative electrode side, two circuits are required for inverter circuits of the power sources, and it is necessary to provide two pairs of (four) electric power supply lines. For example, in a case where the main body part of the above-described portable radiation irradiation devices are provided with the inverter circuits, it is necessary to extend the electric power supply lines within the arm part. However, there is a problem in that the degree of freedom of movement of the arm part becomes low if the four electric power supply lines are extended. Particularly, in a case where an attempt to transmit a voltage of several 10 kV is made, there is a problem in that the coating of the electric power supply lines becomes thick, and flexibility is lost.

Additionally, a method of transmitting a relatively low voltage within the arm part and boosting the voltage on the radiation source side is considered. In such a configuration, the coating of the electric power supply lines can be made thin. However, a current becomes large, and thus it is necessary to make conducting wires thick. Even in a case where four such thick conducting wires are extended, there is a problem in that the degree of freedom of movement of the arm part becomes low.

Additionally, since the inverter circuits generate common mode noise when performing switching, in order to suppress this noise, it is necessary to provide noise suppression components, such as at least two ferrite cores, for the positive electrode side electric power supply lines and the negative electrode side electric power supply lines.

In addition, in JP1986-016498A (JP-S61-016498A), JP2012-243730A, JP2010-244834A, JP2002-175900A, and JP1993-315089A (JP-H05-315089A), using a three-phase or multiphase alternating voltage is suggested as a method of supplying the high voltage to the X-ray tube. However, no methods of solving the problem regarding the degree of freedom of movement of the arm part as described above are suggested.

In view of the above problems, an object thereof is to provide a radiation irradiation device that can improve the degree of freedom of an arm part and can reduce the number of noise suppression components, such as a ferrite core.

A radiation irradiation device of the invention includes a radiation generating part having a radiation source that generates radiation; an arm part having the radiation generating part attached to one end thereof; and a main body part having the other end of the arm part connected thereto. The main body part has a power source part including a three-phase inverter circuit. The power source part supplies a three-phase alternating current voltage to the radiation generating part via the arm part.

Additionally, in the radiation irradiation device of the above invention, the radiation generating part can have two transformer circuits that generate two-system single-phase alternating voltages from the three-phase alternating current voltage, and the two transformer circuits can be respectively provided as separate systems on a positive side and a negative side of the radiation source.

Additionally, in the radiation irradiation device of the above invention, the two transformer circuits of the radiation generating part can be booster circuits.

Additionally, in the radiation irradiation device of the above invention, the two transformer circuits of the radiation generating part can be each provided with a rectifier circuit.

Additionally, in the radiation irradiation device of the above invention, the rectifier circuit that is provided at each of the two transformer circuits can be a voltage doubler rectifier circuit.

Additionally, in the radiation irradiation device of the above invention, the power source part can include a DC power source.

Additionally, in the radiation irradiation device of the above invention, the DC power source can have a lithium ion battery.

According to the radiation irradiation device of the invention, the main body part is provided with the power source part including the three-phase inverter circuit, and the three-phase alternating current voltage is supplied to the radiation generating part via the arm part by the three-phase inverter circuit of the power source part. Thus, the number of electric power supply lines can be reduced from four to three, and the degree of freedom of movement of the arm part in which the electric power supply lines are extended can be improved.

Additionally, as compared to a case where two inverter circuits are used, the number of switching elements can be reduced, and power loss can be reduced.

Additionally, by using the three-phase alternating current voltage, an unbalanced current (common mode current) can be reduced, and unnecessary radiation (Electromagnetic Interference (EMI)) can be reduced.

Additionally, as compared to a case where two inverter circuits are used, the number of insulated transformers can be reduced by half, and thereby, size and weight reduction become possible.

Additionally, as compared to a case where two inverter circuits are used, a controller for the inverter circuits can be simplified, and cost can be reduced.

DESCRIPTION OF THE PREFERRED EMBODIMENTS

Figure 1:
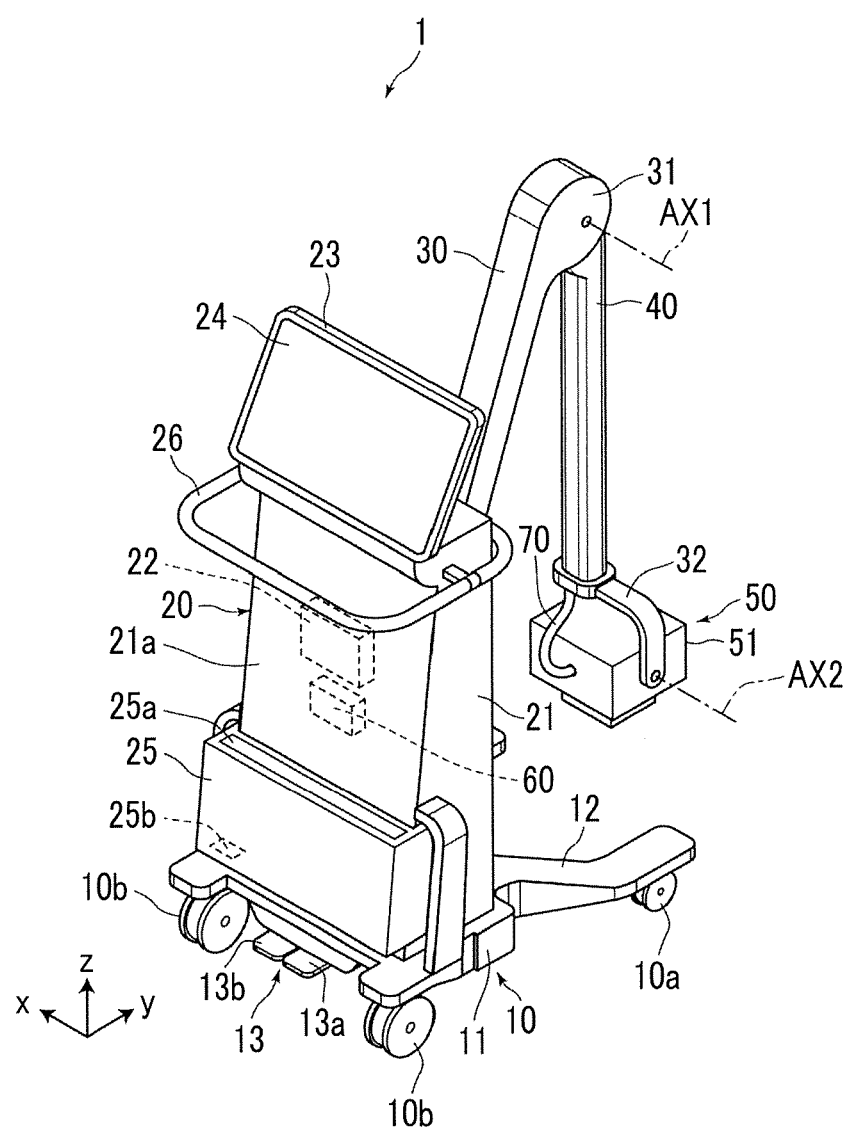
FIG. 1 is a perspective view illustrating an entire shape of a radiation irradiation device of an embodiment of the invention.
Figure 2:
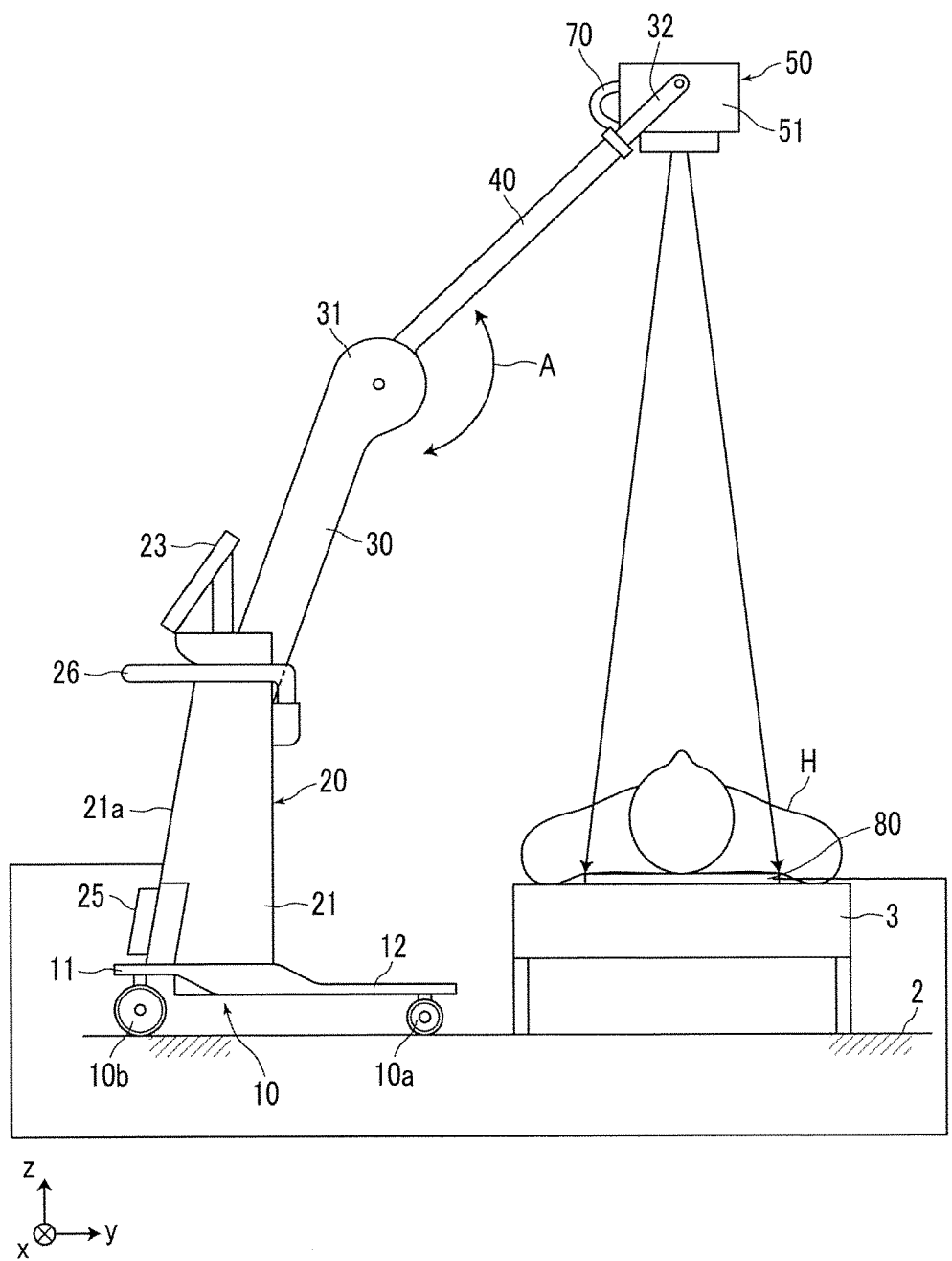
FIG. 2 is a view illustrating the state when the radiation irradiation device of the embodiment of the invention is used.

Hereinafter, a radiation irradiation device of an embodiment of the invention will be described in detail, referring to the drawings. Although the invention has features in the configuration of electric power supply to the radiation generating part in the radiation irradiation device, the entire configuration of the radiation irradiation device will first be described. FIG. 1 is a perspective view illustrating the entire shape of the radiation irradiation device of the present embodiment when being not used, and FIG. 2 is a side view illustrating the state when the radiation irradiation device of the present embodiment is used. In addition, in the following, an upper side and a lower side in the vertical direction in a state where the radiation irradiation device is placed on, for example, a device placement surface, such as a floor of a medical institution, are referred to as "up" and "down", respectively, and a direction perpendicular to the vertical direction in the same state is referred to as a "horizontal" direction. Additionally, in the views to be described below, the vertical direction is defined as a z direction, a leftward-rightward direction of the radiation irradiation device is defined as an x direction, and a forward-backward direction of the radiation irradiation device is defined as a y direction. In addition, the front herein means a side to which an arm part extends from a main body part of the radiation irradiation device when the device is used.

As illustrated in FIGS. 1 and 2, a radiation irradiation device 1 of the present embodiment includes a leg part 10, a main body part 20, a supporting member 30, an arm part 40, and a radiation generating part 50.

Figure 3:
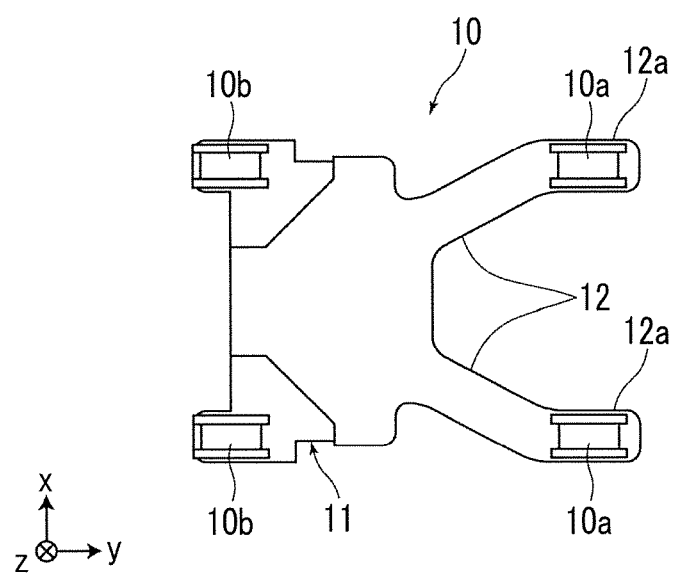
FIG. 3 is a view of a leg part as seen from below.

The leg part 10 is capable of traveling on a device placement surface 2, and consists of a plate-shaped pedestal part 11 on which the main body part 20 is placed, and a foot arm part 12 that extends from the pedestal part 11 toward the front. FIG. 3 is a view of the leg part 10 as seen from below. As illustrated in FIG. 3, the foot arm part 12 is formed in a V shape that widens in the leftward-rightward direction toward the front. First casters 10a are respectively provided on bottom surfaces of two tip parts 12a at the front of the foot arm part 12, and second casters 10b are respectively provided on bottom surfaces of two corners at the rear of the pedestal part 11. By forming the foot arm part 12 in a V shape as described above, for example, as compared to a case where the entire leg part 10 is formed in a rectangular shape, an edge part of the leg part does not easily collide against its surrounding obstacle when the leg part 10 is rotated. Thus, handling can be made easy. Additionally, weight reduction can also be achieved.

Each first caster 10a has a shaft that extends in the upward-downward direction, and is attached to the foot arm part 12 such that a rotating shaft of a wheel is revolvable within a horizontal plane about the shaft of the first caster. Additionally, each second caster 10b also has a shaft that extends in the upward-downward direction, and is attached to the pedestal part 11 such that a rotating shaft of a wheel is revolvable within the horizontal plane about the shaft of the second caster. In addition, the rotating shaft of each wheel herein is a rotating shaft when the wheel rotates and travels. The leg part 10 is configured so as to be capable of traveling in an arbitrary direction on the device placement surface 2 by the first casters 10a and the second casters 10b.

Additionally, as illustrated in FIG. 1, a pedal part 13 is provided at the rear of the leg part 10. The pedal part 13 consists of two pedals of a first pedal 13a and a second pedal 13b. The first pedal 13a is a pedal for bringing the second casters 10b into a non-revolvable state. As a user steps on the first pedal 13a, the second casters 10b are configured so as to be locked in revolution by a locking mechanism and brought into the non-revolvable state.

Additionally, the second pedal 13b is a pedal for bringing the second casters 10b into a revolvable state from the non-revolvable state. As the user steps on the second pedal 13b, the second casters 10b are configured so as to be released from the locking by the locking mechanism and brought into the revolvable state again.

A well-known configuration can be used as the locking mechanism that locks the revolution of the second casters 10b. For example, the revolution may be locked such that both sides of the wheels of the second casters 10b are sandwiched by plate-shaped members, or the revolution may be locked by providing members that stop the rotation of shafts of the second caster 10b that extend in the upward-downward direction.

The main body part 20 is placed on the pedestal part 11 of the leg part 10, and includes a housing 21. A control part 22 that controls driving of the radiation irradiation device 1 and a power source part 60 are housed within the housing 21.

The control part 22 performs control regarding generation and irradiation of radiation, such as a tube current, irradiation time, and a tube voltage, in the radiation generating part 50, and control regarding acquisition of radiation images, such as image processing of a radiation image acquired by the radiation detector to be described below. The control part 22 is configured of, for example, a computer in which a program for control is installed, exclusive hardware, or combination of both.

The power source part 60 supplies electric power to the radiation generating part 50, a monitor 23, and the radiation detector housed within a cradle 25 to be described below. In addition, the monitor 23 may be configured so as to be attachable to and detachable from the main body part 20. In that case, the power source part 60 supplies electric power to a battery built in the monitor 23 to charge the battery. Additionally, the radiation detector also has a battery built therein, and the power source part 60 supplies electric power to the built-in battery to charge the battery.

Figure 4:
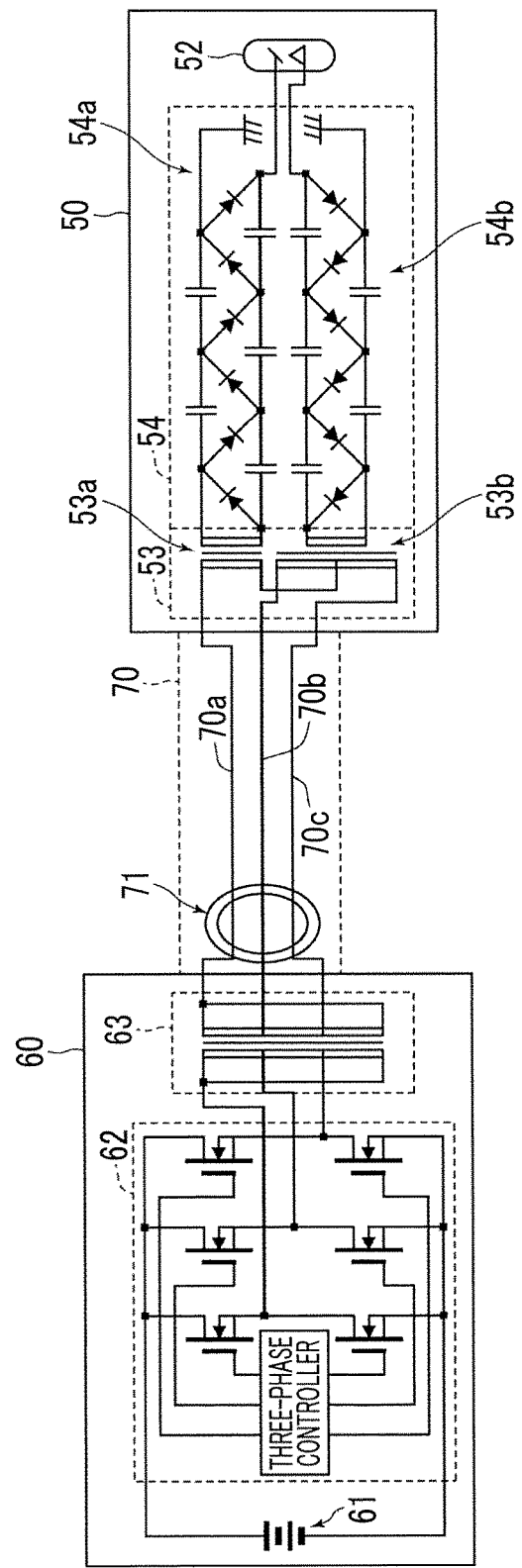
FIG. 4 is a schematic view illustrating an electrical configuration of a power source part and a radiation generating part.

FIG. 4 is a schematic view illustrating an electrical configuration of the power source part 60 and the radiation generating part 50. As illustrated in FIG. 4, the power source part 60 includes a battery part 61, a three-phase inverter circuit 62, and an insulated transformer 63.

The battery part 61 includes a plurality of lithium ion batteries. The plurality of lithium ion batteries may be connected in series, or may be connected in parallel. The lithium ion batteries are a cell formed by connecting a plurality of lithium ion batteries in series and in parallel. In addition, in the present embodiment, the lithium ion batteries are used from a viewpoint that weight reduction and handling are easy. However, the invention is not limited, and batteries consisting of nickel hydrogen batteries, batteries consisting of NaS batteries, batteries consisting of fuel cells, and the like can be used.

The battery part 61 of the present embodiment outputs a voltage of 48 V. Although the voltage output from the battery part 61 is not limited to 48 V, it is desirable that the voltage is 60 V or less. By setting the voltage to 60 V or less, an insulation creepage space distance can be made small, and size reduction can be achieved.

The three-phase inverter circuit 62 converts a direct current voltage output from the battery part 61 into a three-phase alternating voltage. Specifically, as illustrated in FIG. 4, the three-phase inverter circuit 62 includes six switching elements, and a three-phase controller that controls the switching elements. In addition, the circuit configuration of the three-phase inverter circuits is not limited to the circuit configuration illustrated in FIG. 4, and other well-known three-phase inverter circuits may be adopted.

The insulated transformer 63 transmits a three-phase alternating voltage of 48 V output from the three-phase inverter circuit 62 to a cable part 70.

In addition, the battery part 61 is connected to an external power source via a connector (not illustrated), and is charged under the supply of electric power from the external power source.

The three-phase alternating voltage output from the power source part 60 is supplied to the radiation generating part 50 via the cable part 70. The cable part 70 electrically connects the power source part 60 provided within the main body part 20 and the radiation generating part 50 provided at the tip of the arm part 40 to each other, and includes three electric power supply wiring lines 70a, 70b, and 70c with which alternating voltages of respective phases are supplied, respectively. Each of the electric power supply wiring lines 70a to 70c is formed by covering a conductive member with an insulating member, and extends inside the supporting member 30 and inside the arm part 40. The length of the cable part 70 is, for example, about 3 m and the wiring electrical resistance of the cable part is, for example, about 75 mΩ. Additionally, although not illustrated, the cable part 70 includes a control signal wiring line that supplies a control signal output from the control part 22 to the radiation generating part 50, in addition to the electric power supply wiring lines 70a to 70c.

Additionally, the three electric power supply wiring lines 70a to 70c and the control signal wiring line are provided with one ferrite core 71.

The radiation generating part 50 is a so-called mono-tank in which a radiation source, a booster circuit, a voltage doubler rectifier circuit, and the like are provided within the housing 51 (refer to FIG. 1). As illustrated in FIG. 4, the radiation generating part 50 of the present embodiment includes an X-ray tube 52 serving as a radiation source, a booster circuit part 53, and a voltage doubler rectifier circuit part 54.

The booster circuit part 53 boosts the three-phase alternating voltage input via the cable part 70, and generates two-system single-phase alternating voltages. Specifically, the booster circuit part 53 includes a positive electrode side transformer circuit 53a and a negative electrode side transformer circuit 53b. The positive electrode side transformer circuit 53a and the negative electrode side transformer circuit 53b of the present embodiment boost the input alternating voltage to, for example, a single-phase alternating voltage of 200 times or more. The positive electrode side transformer circuit 53a and the negative electrode side transformer circuit 53b of the present embodiment boost the alternating voltage of 48 V to a single-phase alternating voltage of 10 kV.

The voltage doubler rectifier circuit part 54 doubles and rectifies the two-system single-phase alternating voltages output from the booster circuit part 53. Specifically, the voltage doubler rectifier circuit part 54 includes a positive electrode side voltage doubler rectifier circuit 54a and a negative electrode side voltage doubler rectifier circuit 54b. The positive electrode side voltage doubler rectifier circuit 54a doubles and rectifies the single-phase alternating voltage output from the positive electrode side transformer circuit 53a, and rectifies the alternating voltage to, for example, a positive direct current voltage of 5 times. The positive electrode side voltage doubler rectifier circuit 54a of the present embodiment rectifies the single-phase alternating voltage of 10 kV boosted by the positive electrode side transformer circuit 53a to a direct current voltage of 50 kV.

Meanwhile, the negative electrode side voltage doubler rectifier circuit 54b doubles and rectifies the single-phase alternating voltage output from the negative electrode side transformer circuit 53b, and rectifies the alternating current to, for example, a negative direct current voltage of 5 times, similar to the positive electrode side voltage doubler rectifier circuit 54a. The negative electrode side voltage doubler rectifier circuit 54b of the present embodiment rectifies the alternating voltage of 10 kV boosted by the negative electrode side transformer circuit 53b to a direct current voltage of −50 kV. In addition, the specific circuit configuration of the voltage doubler rectifier circuit part 54 is not limited to the circuit configuration illustrated in FIG. 4, and various well-known circuit configurations can be adopted.

The X-ray tube 52 generates radiation by applying a direct current voltage output from the voltage doubler rectifier circuit part 54. In the present embodiment, as described above, the direct current voltage of 50 kV is supplied to a positive electrode side of the X-ray tube 52 by the positive electrode side voltage doubler rectifier circuit 54a, and the direct current voltage of −50 kV is supplied to a negative electrode side of the X-ray tube 52 by the negative electrode side voltage doubler rectifier circuit 54b. As a result, the direct current voltage of 100 kV is applied to the X-ray tube 52.

Emission of the radiation from the X-ray tube 52 of the radiation generating part 50 is performed by an operator's instruction from an input part 24 in the monitor 23.

Returning to FIGS. 1 and 2, an L-shaped radiation source attachment part 32 is provided at a tip (one end) of the arm part 40. The radiation generating part 50 is attached to the one end of the arm part 40 via the radiation source attachment part 32. As illustrated in FIGS. 1 and 2, the cable part 70 taken out from the one end of the arm part 40 is connected to the radiation generating part 50 via a connector.

The radiation generating part 50 is connected to the radiation source attachment part 32 so as to be rotationally movable with an axis AX2 as a rotational movement axis. The rotational movement axis AX2 is an axis that extends in the leftward-rightward direction (x direction). In addition, the radiation source attachment part 32 holds the radiation generating part 50 such that the radiation generating part 50 moves rotationally via a friction mechanism. For this reason, the radiation generating part 50 is rotationally movable by applying a certain degree of strong external force, does not move rotationally unless an external force is applied, and maintains a relative angle with respect to the arm part 40.

Figure 5:
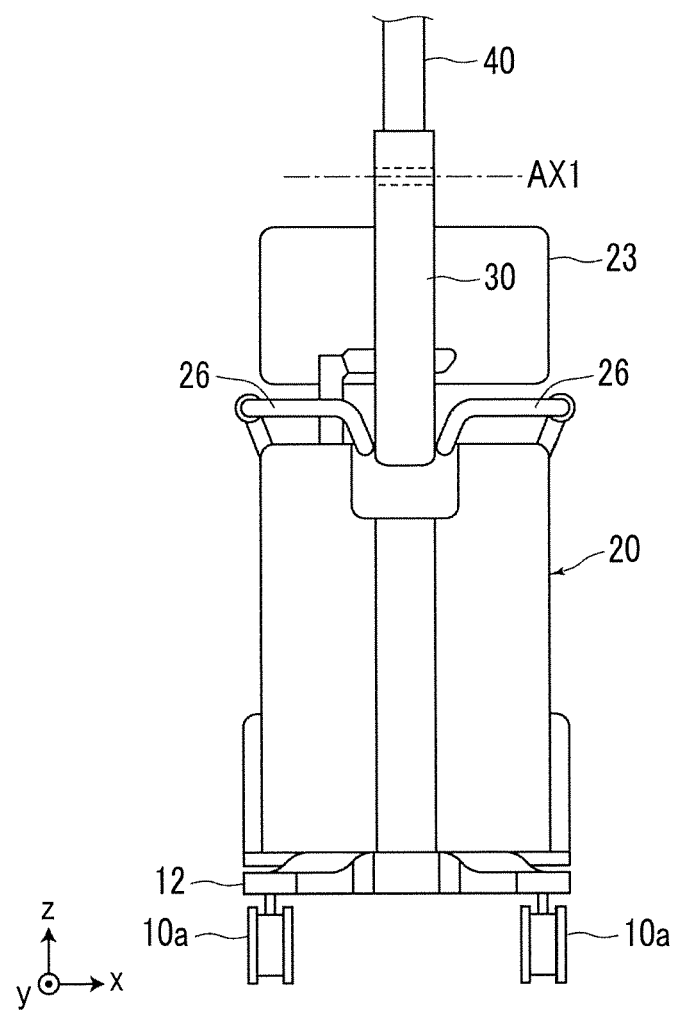
FIG. 5 is a view of the radiation irradiation device illustrated in FIG. 1 as seen from the front.

Additionally, the monitor 23 is attached to an upper surface of the housing 21. Additionally, a handle part 26 for pushing or pulling the radiation irradiation device 1 is attached to an upper part of the housing 21. The handle part 26 is provided so as to go around the housing 21, and is configured so as to be capable of being held not only from a rear side of the radiation irradiation device 1 but also from a front side or a lateral side. FIG. 5 is a view of the radiation irradiation device 1 as seen from the front. As illustrated in FIG. 5, the handle part 26 is provided so as to go around to a front side of the main body part 20.

The monitor 23 consists of a liquid crystal panel or the like, and displays a radiation image acquired by imaging of a subject, and various kinds of information required for the control of the radiation irradiation device 1. Additionally, the monitor 23 includes the touch panel type input part 24, and receives input of various instructions required for the operation of the radiation irradiation device 1. Specifically, input for setting of imaging conditions and input for imaging, that is, emission of radiation, is received. The monitor 23 is attached to the upper surface of the housing 21 so as to be capable of changing the inclination and the rotational position of a display surface with respect to the horizontal direction. Additionally, instead of the touch panel type input part 24, buttons for performing various operations may be included as the input part.

One end of the supporting member 30 is connected to the other end of the a in part 40. The arm part 40 is connected to the supporting member 30 so as to be rotationally movable with an axis AX1 as a rotational movement axis. The rotational movement axis AX1 is an axis that extends in the leftward-rightward direction (x direction). The arm part 40 moves rotationally in a direction of arrow A illustrated in FIG. 2 such that an angle formed with the supporting member 30 is changed about the rotational movement axis AX1.

A rotational movement part 31 having the rotational movement axis AX1 holds the arm part 40 such that the arm part 40 moves rotationally via the friction mechanism. For this reason, the arm part 40 is rotationally movable by applying a certain degree of strong external force, does not move rotationally unless an external force is applied, and maintains a relative angle with respect to the supporting member 30.

In addition, although the rotational movement of the arm part 40 and the radiation generating part 50 is performed via the friction mechanism, rotational movement positions of these parts may be fixed by a well-known locking mechanism. In this case, the rotational movements of the arm part 40 and the radiation generating part 50 become possible by releasing the locking mechanism. The rotational movement positions can be fixed by locking the locking mechanism at desired rotational movement positions.

The other end of the supporting member 30 is connected to the surface of the main body part 20 on the front side. The supporting member 30 is provided so as to be fixed with respect to the main body part 20, and is attached so as to be non-rotatable with respect to the main body part 20. In the present embodiment, as described above, the orientation of the arm part 40 can be freely changed together with the main body part 20 by the revolution of the first casters 10a and the second casters 10b. Thus, it is not necessary to make the supporting member 30 have a degree of freedom, and a simpler configuration can be adopted. However, the invention is not limited to this, and the supporting member 30 may be configured to rotate with emphasis on handleability. That is, the supporting member 30 may be configured so as to be rotatable with an axis passing through the center of the portion of the supporting member 30 connected to the main body part 20 and extending in the vertical direction as a rotation axis.

In the present embodiment, when a subject is imaged, as illustrated in FIG. 2, the imaging is performed by arranging a radiation detector 80 under a subject H that lies on ones' back on a bed 3 and irradiating the subject H with the radiation emitted from the radiation generating part 50. In addition, the radiation detector 80 and the radiation irradiation device 1 are connected together with or without wires. Accordingly, the radiation image of the subject H acquired by the radiation detector 80 is directly input to the radiation irradiation device 1.

Figure 6:
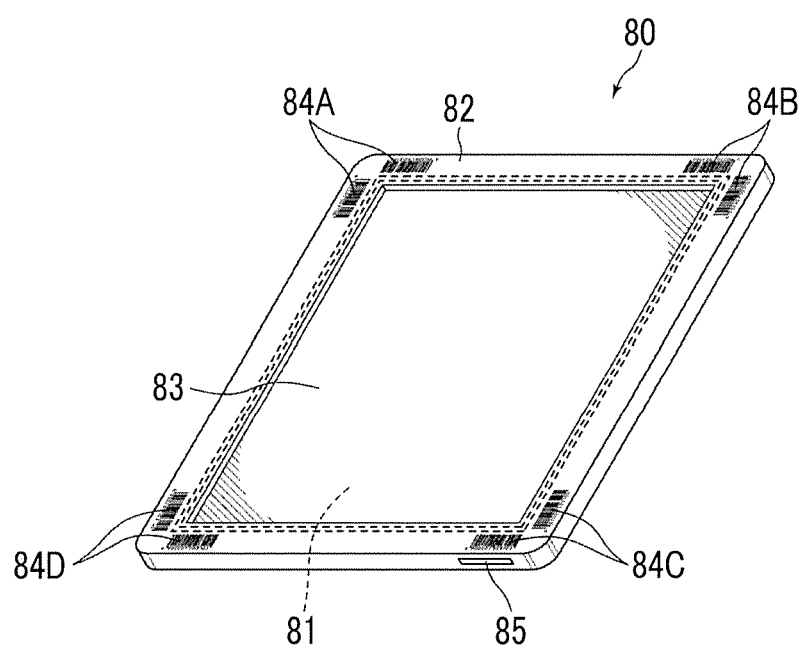
FIG. 6 is an external perspective view of a radiation detector as seen from a radiation detection surface side.

Here, a radiation detector 80 will be briefly described with reference to FIG. 6. FIG. 6 is an external perspective view of the radiation detector as seen from a front surface that is a radiation detection surface side. As illustrated in FIG. 6, the radiation detector 80 is a cassette type radiation detector including a housing 82 that has a rectangular flat plate shape and houses a detecting part 81. The detecting part 81 includes a scintillator (fluorescent body) that converts incident radiation into visible light as is well known, and a thin film transistor (TFT) active matrix substrate. A rectangular imaging region where a plurality of pixels that accumulate electrical charge according to the visible light from the scintillator are arrayed is formed on the TFT active matrix substrate.

Additionally, the housing 82 includes a round-chamfered metallic frame. A gate driver that gives a gate pulse to a gate of a TFT to switch the TFT, an imaging control part including a signal processing circuit that converts an electrical charge accumulated in a pixel into an analog electrical signal representing an X-ray image to output the converted signal, and the like in addition to the detecting part 81 are built in the housing. Additionally, the housing 82 has, for example, a size based on International Organization for Standardization (ISO) 4090:2001 that is substantially the same as a film cassette, an imaging plate (IP) cassette, and a computed radiography (CR) cassette.

A transmission plate 83 that allows radiation to be transmitted therethrough is attached to a front surface of the housing 82. The transmission plate 83 has a size that substantially coincides with a detection region of radiation in the radiation detector 80, and is formed of a carbon material that is lightweight, has high rigidity, and has high radiation transmissivity. In addition, the shape of the detection region is the same oblong shape as the shape of the front surface of the housing 82. Additionally, the portion of the frame of the housing 82 protrudes from the transmission plate 83 in a thickness direction of the radiation detector 80. For this reason, the transmission plate 83 is not easily damaged.

Markers 84A to 84D showing identification information for identifying the radiation detector 80 are applied to four corners of the front surface of the housing 82. In the present embodiment, the markers 84A to 84D consist of two bar codes that are orthogonal to each other, respectively.

Additionally, a connector 85 for charging the radiation detector 80 is attached to a side surface of the housing 82 on the markers 84C, 84D side.

When the radiation irradiation device 1 according to the present embodiment is used, the operator rotationally moves the arm part 40 around the rotational movement axis AX1 in an illustrated counterclockwise direction from an initial position of the arm part 40 illustrated in FIG. 1, and thereby the radiation generating part 50 is moved to a target position immediately above the subject H, as illustrated in FIG. 2. The radiation image of the subject H can be acquired by driving the radiation generating part 50 according to an instruction from the input part 24 to irradiate the subject H with radiation and detecting the radiation transmitted through the subject H, using the radiation detector 80, after the radiation generating part 50 is moved to the target position.

In addition, as the radiation detector 80, as described above, it is desirable to use a radiation detector in which the scintillator and the TFT active matrix substrate including light receiving elements are laminated and which receives irradiation of radiation from a TFT active matrix substrate side (a side opposite to a scintillator side). By using such a high-sensitivity radiation detector 80, a low-output radiation source can be used as the radiation generating part 50, and the weight of the radiation generating part 50 can be made light. In addition, generally, the radiation source output of the radiation generating part 50 and the weight of the radiation generating part 50 are in a proportional relation.

Since the weight of the radiation generating part 50 can be made light as described above, the total weight of the radiation irradiation device 1 can also be made light. Accordingly, by using the revolving casters as the second caster 10b (rear wheels) as in the radiation irradiation device 1 of the present embodiment, the revolution performance of the radiation irradiation device 1 can be improved, and handling can be markedly improved.

In addition, the radiation source output of the radiation generating part 50 is preferably 15 kW or less, and is more preferably 4 kW or less. Additionally, the total weight of radiation irradiation device 1 is preferably 120 kg or less, and is more preferably 90 kg or less.

Next, a configuration in which the radiation detector 80 in the main body part 20 is capable of being housed will be described. As illustrated in FIGS. 1 and 2, the housing 21 of the main body part 20 has a flat surface 21a inclined to a supporting member 30 side, on a surface opposite to a side where the supporting member 30 is attached, and the flat surface 21a is provided with the cradle 25.

An insertion port 25a for inserting the radiation detector 80 is formed in an upper surface of the cradle 25. The insertion port 25a has an elongated shape of a size such that the radiation detector 80 is fitted thereto. In the present embodiment, one end part on a side having the connector 85 of the radiation detector 80 is inserted to the insertion port 25a. Accordingly, this one end part is supported by a bottom part of the cradle 25, and the radiation detector 80 is held by the cradle 25. In this case, a front surface of the radiation detector 80 is directed to a flat surface 21a side.

A connector 25b is attached to the bottom part of the cradle 25. The connector 25b is electrically connected to the connector 85 of the radiation detector 80 when the radiation detector 80 is held by the cradle 25. The connector 25b is electrically connected to the battery part 61 of the power source part 60. Hence, when the radiation detector 80 is held by the cradle 25, the radiation detector 80 is charged by the battery part 61 via the connector 85 of the radiation detector 80 and the connector 25b of the cradle 25.

In addition, a configuration in which the radiation detector 80 is chargeable by the battery part 61 has been described in the present embodiment. As described above, a configuration in which the monitor 23 is chargeable by the battery part 61 may be adopted. Moreover, a configuration in which an external connector is further provided at the main body part 20 and external instruments other than the monitor are connectable may be adopted. Also, a configuration in which electric power is supplied to an external instrument by the battery part 61 via the external connector and the external instrument is chargeable may be adopted. As the external instrument, for example, there is a note-type computer used as a console, or the like.

In addition, the radiation irradiation device of the invention does not necessarily include the leg part 10 as in the radiation irradiation device 1 of the above embodiment. Additionally, the configuration of the supporting member 30 and the arm part 40 is not limited to the configuration of the above embodiment, and other configurations may be adopted.

EXPLANATION OF REFERENCES

1: radiation irradiation device
2: device placement surface
3: bed
10: leg part
10a: first caster
10b: second caster
11: pedestal part
12: foot arm part
12a tip part
13: pedal part
13a: first pedal
13b: second pedal
20: main body part
21: housing
21a: flat surface
22: control part
23: monitor
24: input part
25: cradle
25a: insertion port
25b: connector
26: handle part
30: supporting member
31: rotational movement part
32: radiation source attachment part 40: arm part
50: radiation generating part
51: housing
52: X-ray tube
53: booster circuit part
53a positive electrode side transformer circuit
53b negative electrode side transformer circuit
54: voltage doubler rectifier circuit part
54a: positive electrode side voltage doubler rectifier circuit
54b: negative electrode side voltage doubler rectifier circuit
60: power source part
61: battery part
62: three-phase inverter circuit
63: insulated transformer
70: cable part
70a to 70c: electric power supply wiring line
71: ferrite core
80: radiation detector
81: detecting part
82: housing
83: transmission plate
84A to 84D: marker
85: connector
AX1: rotational movement axis
AX2: rotational movement axis
H: subject

What is claimed is:

1. A radiation irradiation device comprising:
a radiation generating part having a radiation source that generates radiation;
an arm part having the radiation generating part attached to one end thereof; and
a main body part having the other end of the arm part connected thereto,
a power source part having a three-phase inverter circuit, wherein the power source part is provided at the main body, and
a cable part for electrically connecting the three-phase inverter circuit and the radiation generating part;
wherein the three-phase inverter circuit supplies a three-phase alternating current voltage to the radiation generating part via the cable part which is extended along the arm part,
wherein the radiation generating part has two transformer circuits that generate two-system single-phase alternating voltages from the three-phase alternating current voltage, and the two transformer circuits are respectively provided as separate systems on a positive side and a negative side of the radiation source.

2. The radiation irradiation device according to claim 1, wherein the two transformer circuits of the radiation generating part are booster circuits.

3. The radiation irradiation device according to claim 2, wherein the two transformer circuits of the radiation generating part are each provided with a rectifier circuit.

4. The radiation irradiation device according to claim 3, wherein the power source part includes a DC power source.

5. The radiation irradiation device according to claim 4, wherein the DC power source has a lithium ion battery.

6. The radiation irradiation device according to claim 2, wherein the power source part includes a DC power source.

7. The radiation irradiation device according to claim 6, wherein the DC power source has a lithium ion battery.

8. The radiation irradiation device according to claim 1, wherein the two transformer circuits of the radiation generating part are each provided with a rectifier circuit.

9. The radiation irradiation device according to claim 8, wherein the rectifier circuit that is provided at each of the two transformer circuits is a voltage doubler rectifier circuit.

10. The radiation irradiation device according to claim 9, wherein the power source part includes a DC power source.

11. The radiation irradiation device according to claim 10, wherein the DC power source has a lithium ion battery.

12. The radiation irradiation device according to claim 8, wherein the power source part includes a DC power source.

13. The radiation irradiation device according to claim 12, wherein the DC power source has a lithium ion battery.

14. The radiation irradiation device according to claim 1, wherein the power source part includes a DC power source.

15. The radiation irradiation device according to claim 14, wherein the DC power source has a lithium ion battery.

* * * * *